(12) United States Patent
Farazi et al.

(10) Patent No.: US 7,676,275 B1
(45) Date of Patent: Mar. 9, 2010

(54) ENDOVASCULAR LEAD FOR CHRONIC NERVE STIMULATION

(75) Inventors: Taraneh Ghaffari Farazi, San Jose, CA (US); Timothy A. Fayram, Gilroy, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 226 days.

(21) Appl. No.: 11/120,345

(22) Filed: May 2, 2005

(51) Int. Cl.
  *A61N 1/05* (2006.01)
  *A61N 1/18* (2006.01)
(52) U.S. Cl. .......................... 607/127; 607/122; 607/9; 607/148
(58) Field of Classification Search .................... 607/2, 607/9, 18, 74, 122, 127, 131, 148, 116, 119, 607/125, 149; 600/372, 377, 4
See application file for complete search history.

(56) References Cited

U.S. PATENT DOCUMENTS

| | | | |
|---|---|---|---|
| 3,774,618 A | 11/1973 | Avery | |
| 4,860,769 A | 8/1989 | Fogarty et al. | |
| 4,934,368 A * | 6/1990 | Lynch | 607/2 |
| 5,170,802 A | 12/1992 | Mehra | 128/784 |
| 5,224,491 A | 7/1993 | Mehra | 128/784 |
| 5,231,988 A | 8/1993 | Wernicke et al. | |
| 5,251,634 A * | 10/1993 | Weinberg | 600/377 |
| 5,320,643 A | 6/1994 | Roline | |
| 5,330,507 A | 7/1994 | Schwartz | |
| 5,387,233 A | 2/1995 | Alferness et al. | |
| 5,411,546 A | 5/1995 | Bowald et al. | |
| 5,441,521 A | 8/1995 | Hedberg | |
| 5,476,498 A | 12/1995 | Ayers | |
| 5,578,061 A | 11/1996 | Stroetmann et al. | 607/4 |
| 5,658,318 A | 8/1997 | Stroetmann et al. | 607/6 |
| 5,690,681 A | 11/1997 | Geddes | |
| 5,916,239 A | 6/1999 | Geddes | |
| 5,922,014 A * | 7/1999 | Warman et al. | 607/123 |
| 5,978,705 A | 11/1999 | KenKnight | |
| 6,129,750 A | 10/2000 | Tockman et al. | |
| 6,134,470 A | 10/2000 | Hartlaub | |

(Continued)

FOREIGN PATENT DOCUMENTS

EP 0 566 652 B1 6/1994

(Continued)

OTHER PUBLICATIONS

Non-Final Office Action mailed May 28, 2008: Related U.S. Appl. No. 11/283,229.

(Continued)

*Primary Examiner*—Kennedy J. Schaetzle
*Assistant Examiner*—Natasha N Patel
(74) *Attorney, Agent, or Firm*—Steven M. Mitchell; Theresa A. Takeuchi

(57) ABSTRACT

A lead of the present invention comprises an electrode array adapted to be stably anchored at a selected location within the vena cava of a human patient. The electrode array may take various shapes, including helical, annular and linear. The electrode array is connectable to an electrical stimulation means such as an implantable pulse or signal generator. Electrical stimulation applied to a selected region of the vena cava and across the wall of the vein, that is, transvascularly, to the vagus nerve or branches thereof, depolarizes the nerve to thereby effect control of the heart rate.

20 Claims, 5 Drawing Sheets

U.S. PATENT DOCUMENTS

| | | | |
|---|---|---|---|
| 6,157,862 A * | 12/2000 | Brownlee et al. | 607/123 |
| 6,292,695 B1 | 9/2001 | Webster, Jr. et al. | |
| 6,341,236 B1 | 1/2002 | Osorio | |
| 6,349,233 B1 | 2/2002 | Adams | 607/5 |
| 6,564,096 B2 | 5/2003 | Mest | |
| 6,587,727 B2 | 7/2003 | Osorio | |
| 6,615,081 B1 | 9/2003 | Boveja | |
| 6,628,987 B1 | 9/2003 | Hill | |
| 6,671,556 B2 | 12/2003 | Osorio | |
| 6,972,016 B2 * | 12/2005 | Hill et al. | 606/41 |
| 7,031,777 B2 * | 4/2006 | Hine et al. | 607/122 |
| 7,072,720 B2 * | 7/2006 | Puskas | 607/118 |
| 7,321,793 B2 | 1/2008 | Ben Ezra | |
| 2002/0120304 A1 | 8/2002 | Mest | |
| 2002/0123771 A1 | 9/2002 | Ideker et al. | 607/14 |
| 2003/0078623 A1 | 4/2003 | Weinberg | |
| 2003/0181951 A1 | 9/2003 | Cates | 607/9 |
| 2003/0229380 A1 * | 12/2003 | Adams et al. | 607/9 |
| 2004/0019364 A1 | 1/2004 | Kieval | |
| 2004/0172075 A1 | 9/2004 | Shafer | |
| 2005/0065553 A1 | 3/2005 | Ben Ezra | |
| 2005/0143787 A1 | 6/2005 | Boveja | |
| 2005/0149131 A1 | 7/2005 | Libbus | |
| 2006/0173493 A1 * | 8/2006 | Armstrong et al. | 607/2 |
| 2006/0178703 A1 | 8/2006 | Huston | |

FOREIGN PATENT DOCUMENTS

| | | | |
|---|---|---|---|
| EP | 0 566 652 B2 | 11/1997 | |
| EP | 1304135 A2 | 4/2003 | |

OTHER PUBLICATIONS

Non-Final Office Action mailed Oct. 15, 2008: Related U.S. Appl. No. 11/120,345.

Non-Final Office Action mailed Feb. 26, 2009: Related U.S. Appl. No. 11/120,345.

Non-Final Office Action mailed Jan. 29, 2009: Related U.S. Appl. No. 11/330,884.

Non-Final Office Action mailed Oct. 23, 2008: Related U.S. Appl. No. 11/539,326.

Final Office Action mailed Apr. 7, 2009: Related U.S. Appl. No. 11/539,326.

Final Office Action mailed Dec. 16, 2008: Related U.S. Appl. No. 11/120,345.

Final Office Action mailed Mar. 18, 2009: Related U.S. Appl. No. 11/283,229.

Borovikova et al. "Vagus Nerve Stimulation Attenuates the Systemic Inflammatory Repsonse to Endotoxin" Nature, vol. 405, May 2000.

Borovikova et al. "Role of the Efferent Vagus Nerve Signaling in the Regulation of the Innate Immune Response to LPS" Shock, vol. 13, 2000.

Blum et al "Role of Cytokines in Heart Failure" American Heart Journal, Feb. 1998.

Non-Final Office Action mailed Sep. 19, 2008: Related U.S. Appl. No. 11/330,884.

Non-Final Office Action mailed Jun. 29, 2009: Related U.S. Appl. No. 11/330,884.

* cited by examiner

ENDOVASCULAR LEAD FOR CHRONIC NERVE STIMULATION

FIELD OF THE INVENTION

The present invention relates generally to the management of cardiac rhythm, and particularly to an endovascular medical lead for the transvenous electrical stimulation of the vagus nerve for depressing or inhibiting cardiac arrhythmias such as atrial fibrillation and ventricular tachycardia.

BACKGROUND OF THE INVENTION

The autonomic nervous system controls the involuntary smooth and cardiac muscles and glands throughout the body, serving the vital organ systems such as the heart that function automatically. The two divisions (sympathetic and parasympathetic) of the autonomic nervous system oppose each other in function, thus maintaining balanced activity in the body mechanisms. For example, signals generated in the hypothalamus, cerebral cortex and medulla oblongata within the brain and transmitted via the parasympathetic fibers of the vagus nerve to the sino-atrial node of the heart slow the heart rate while signals along the sympathetic fibers accelerate the heart rate. An imbalance in the relative activity of the sympathetic and parasympathetic divisions of the autonomic nervous system, for example, an increase in the activity of the sympathetic division, can produce abnormal heart rates in the form of tachycardias or fibrillations in either or both chambers (ventricles and/or atria) of the heart.

It is well known that the electrical stimulation of the parasympathetic nerves innervating the heart can restore autonomic nervous system balance by counteracting arrhythmias produced by increased sympathetic activity. Thus, electrical stimulation of the right vagus nerve predominantly slows the S-A node rate and thereby reduces heart rate. The vagus nerve, and particularly cardiovagal branches thereof, are found chiefly adjacent to the posterior surface of the vena cava. Accordingly, parasympathetic activity may be increased to restore autonomic balance by electrically stimulating the fibers of the vagus nerve transvenously by means of an endovascular electrode implanted in, for example, the superior vena cava.

There remains a need for a suitable endovascular, vagus nerve-stimulating lead for chronic use in the areas of discrimination, rate slowing, termination, prediction and prevention. Such a lead would desirably incorporate an array of electrodes adapted to be arranged along the longitudinal direction of the vena cava, with positionally stable placement or anchoring of the electrode array within the vena cava.

SUMMARY OF THE INVENTION

Generally, the lead of the present invention comprises an electrode array adapted to be stably anchored at a selected intravascular location, for example, within the vena cava of a human patient. In accordance with certain embodiments of the invention, the electrode array may take various shapes, including helical, annular and linear. The electrode array is electrically connectable to an electrical stimulation means such as an implantable pulse or signal generator. Electrical stimulation applied to a selected region of the vena cava and across the wall of the vein, that is, transvascularly, to the vagus nerve or branches thereof, depolarizes the nerve to thereby effect control of the heart rate.

In accordance with one, specific, exemplary embodiment of the present invention, there is provided an intravenous lead adapted to electrically stimulate fibers of the vagus nerve in a human patient. That nerve extends along an outer surface of the vena cava. The lead comprises a lead body having a portion along the length thereof adapted to be placed within the vena cava. That portion of the lead body has a generally helical configuration and carries an electrode array comprising a plurality of electrodes adapted to engage an inner surface of the vena cava. Pursuant to one aspect of the invention, the electrode array comprises a plurality of sets of electrodes. Further, the generally helical portion of the lead body may comprise a plurality of turns, each of the turns carrying one of the electrodes of each of the plurality of sets of electrodes. Preferably, the electrodes of each set of electrodes are adapted to be arranged in substantially longitudinal alignment when the helical portion of the lead body is placed within the vena cava. In one particular embodiment, the electrodes comprising each set of electrodes may be electrically connected to be alternately poled. For example, each set of electrodes may comprise three electrodes electrically connected in double bipolar fashion. Preferably, upon placement of the lead body in the vena cava, the mentioned portion of the lead body is expandable into its generally helical configuration so as to engage the inner surface of the vena cava vein and anchor the lead body portion within the vena cava. According to yet another feature of the invention, there is provided a distal section extending distally from the helical portion of the lead body, the distal section carrying at least one electrode selected from the group consisting of a tip pacing and/or sensing electrode, a ring pacing and/or sensing electrode, a cardioverting electrode and a defibrillating electrode.

In accordance with another specific, exemplary embodiment of the invention, there is provided an intravenous lead for electrically stimulating fibers of the vagus nerve, the lead comprising a lead body having a proximal end adapted to be electrically connected to a medical device for generating electrical stimulation signals. The lead body further comprises a distal end portion adapted to be placed within a vein having a wall adjacent to the fibers of the vagus nerve. A plurality of electrodes is carried by the distal end portion of the lead body, the plurality of electrodes being deployable within the vein to form a generally annular electrode array in electrical communication with an inner surface of the wall of the vein and lying in a plane substantially perpendicular to the direction of blood flow within the vein, the plurality of electrodes being electrically connected to the proximal end of the lead body. In one form of this embodiment, each of the plurality of electrodes has a circumferential length, and the circumferential lengths of the plurality of electrodes may be substantially the same. Further, the plurality of electrodes may be substantially uniformly spaced apart. In another form of this embodiment, the plurality of electrodes may be connected in a parallel combination, the parallel combination being connected to the proximal end of the lead body with a single electrical conductor. Alternatively, the plurality of electrodes may be grouped into multiple clusters with the electrodes in each of the multiple clusters being connected in a parallel combination, the parallel combination of electrodes in each cluster being connected to the proximal end of the lead body with a single electrical conductor. Pursuant to another aspect of this embodiment, a distal section may be provided that extends distally from the distal end portion of the lead body, the distal section carrying at least one electrode selected from the group consisting of a tip pacing and/or sensing electrode, a ring pacing and/or sensing electrode, a cardioverting electrode and a defibrillating electrode.

Pursuant to yet another specific, exemplary embodiment of the invention, there is provided an intravenous lead having a portion along the length thereof for placement within the vena cava vein, the vein having a wall comprising an inner surface and an outer surface, the lead being adapted to electrically stimulate fibers of the vagus nerve disposed adjacent to the outer surface of the wall of the vein. The lead comprises a linear array of electrodes disposed along the mentioned portion of the lead and adapted to be placed adjacent to the inner surface of the wall of the vein in alignment with the direction of blood flow within the vein to stimulate the fibers of the vagus nerve when the electrode array is electrically energized. Preferably, the mentioned portion of the lead has attached thereto an anchoring element adapted to engage the inner surface of the wall of the vein. In one form, the anchoring element comprises an expandable ring adapted to lie in a plane perpendicular to the direction of blood flow and engage the inner surface of the wall of the vein when deployed.

BRIEF DESCRIPTION OF THE DRAWINGS

The foregoing and other objects, features and advantages of the invention will become evident to those skilled in the art from the detailed description of the preferred embodiments, below, taken together with the accompanying drawings, in which.

DETAILED DESCRIPTION

The following description presents preferred embodiments of the invention representing the best mode contemplated for practicing the invention. This description is not to be taken in a limiting sense but is made merely for the purpose of describing the general principles of the invention whose scope is defined by the appended claims.

Figure 1:
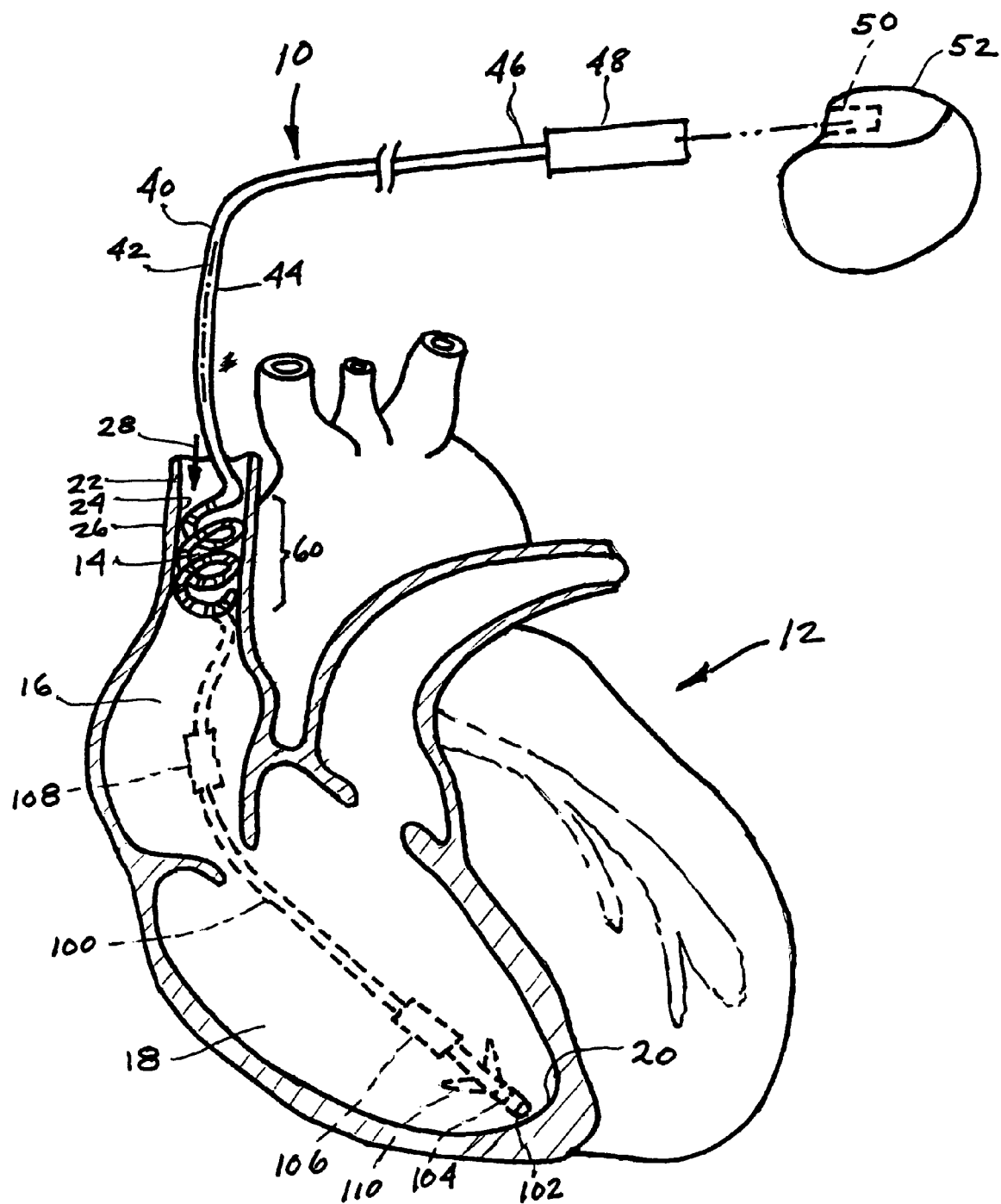
FIG. 1 is a diagrammatic, perspective view of the anterior portion of a human heart showing placed therein an endovascular, vagus nerve-stimulating lead in accordance with one specific exemplary embodiment of the invention.

FIG. 1 shows in solid lines a passive fixation, dedicated nerve stimulation lead 10 for transvenously stimulating a parasympathetic nerve of a mammalian subject, in particular the vagus nerve and cardiovagal branches thereof in a human subject.

Figure 2:
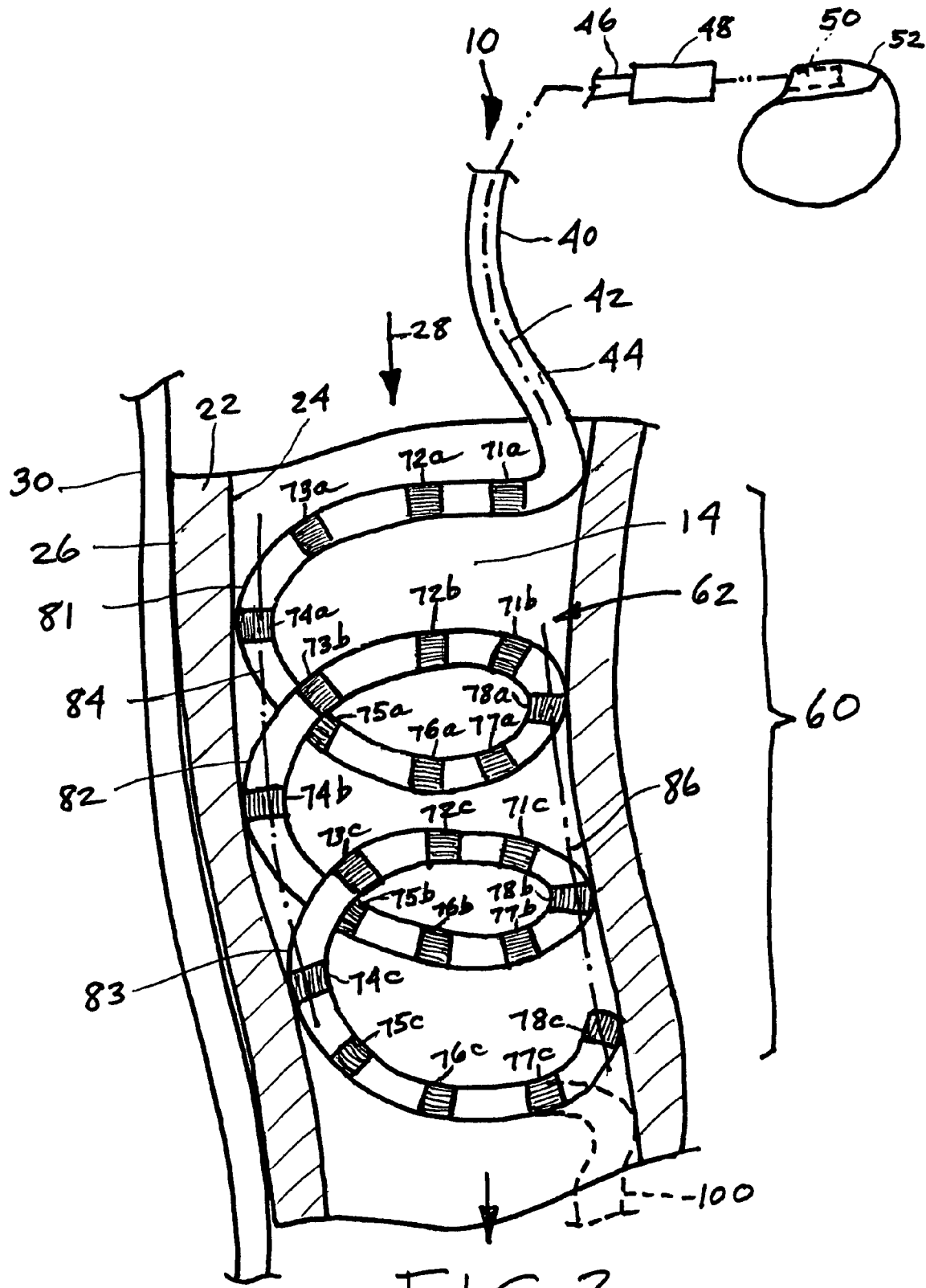
FIG. 2 is an enlargement of a part of FIG. 1 showing, among other things, the details of an electrode array carried by the lead.

FIG. 1 further depicts, in diagrammatic form, the anterior portion of a human heart 12, specifically showing the superior vena cava (SVC) 14 within which a portion of the lead 10 is placed; the right atrium (RA) 16; the right ventricle (RV) 18; and the apex 20 of the RV. The SVC 14 comprises a vessel wall 22 having an inner surface 24 and an outer surface 26. An arrow 28 indicates the direction of venous blood flow toward the RA within the lumen of the SVC. The vagus nerve and its cardiovagal branches, shown diagrammatically in FIG. 2 and identified therein by the reference numeral 30, extends along the posterior of the outer surface 26 of the SVC wall 22.

The lead 10 comprises a lead body 40 having a longitudinal axis 42 and an outer, tubular sheath or housing 44 of a suitable flexible, insulating, biocompatible, biostable material such as, for example, silicone rubber or polyurethane. By way of illustration and not restriction, the lead body 40 may have a diameter ranging from about 0.026 inch (2F) to about 0.156 inch (12F) with a diameter of 0.091 inch (7F) being preferred. The tubular lead body housing 44 may comprise a multilumen member defining, for example, two or more axially or longitudinally extending parallel passages or lumens for carrying electrical conductors and one lumen providing access for a stylet used during lead placement.

The lead body 40 has a proximal end 46 carrying a conventional connector assembly 48 details of which have been omitted but which is configured to be received by one or more receptacles 50 formed in a signal or pulse generator such as an implantable electrical medical device 52. As is known in the art, the connector assembly 48 may comprise a single coaxial component or a multiple branch assembly such as one that is bifurcated or trifurcated. The lead body 40 further comprises a distal end portion 60 having a preformed, generally helical configuration extending about the longitudinal axis 42 of the lead body.

Figure 3:
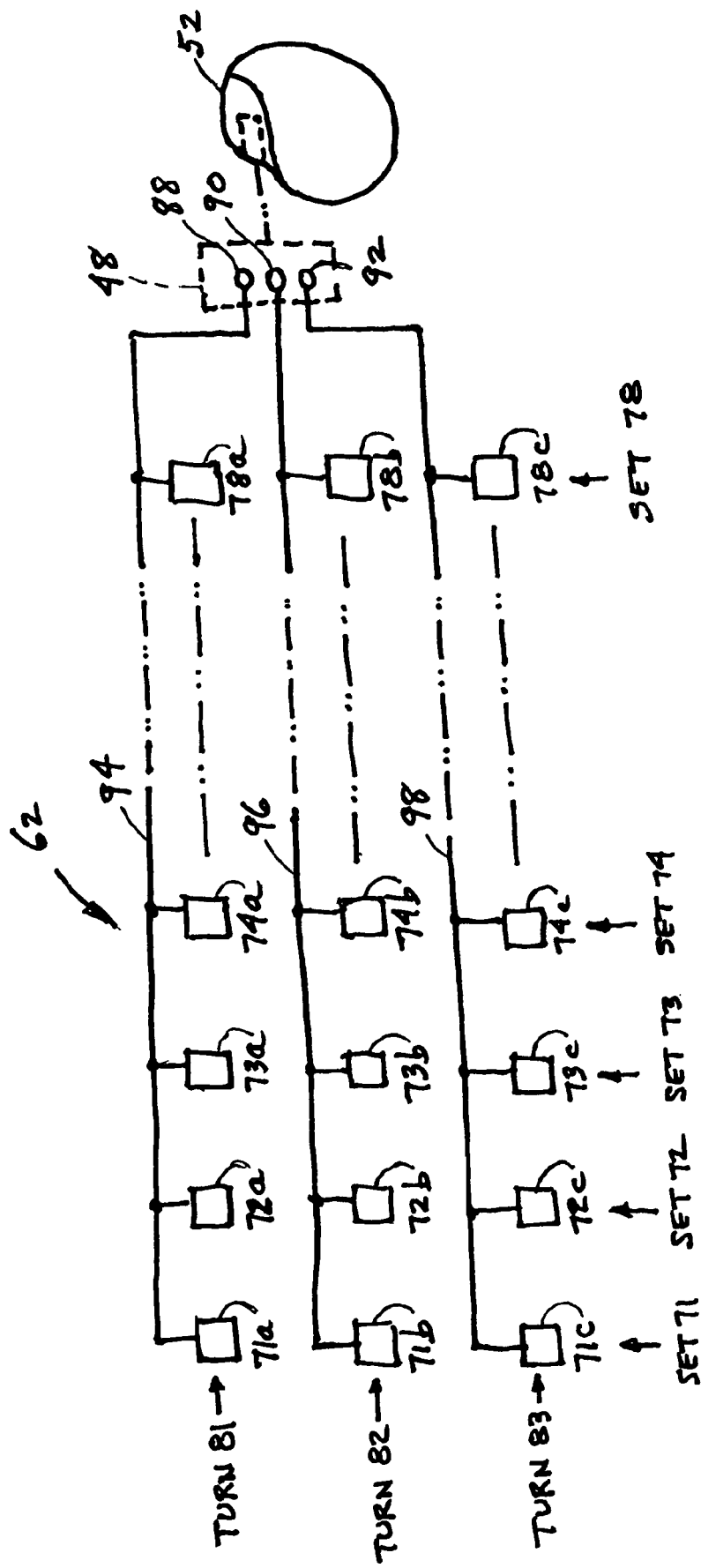
FIG. 3 is a simplified electrical schematic of the lead of FIGS. 1 and 2 showing the manner in which the electrodes of the electrode array are interconnected.

Referring now also to FIG. 3, the helical distal end portion 60 of the lead body carries an electrode array 62 adapted to be placed within the vena cava, and preferably within the SVC 14, of the heart in engagement with the inner surface 24 thereof so as to positionally stabilize or anchor the distal end portion 60. In the embodiment shown, the electrode array 62 may comprise eight electrode sets 71-78 each set comprising three electrodes for a total of twenty-four electrodes. Thus, the electrode set 71 comprises electrodes 71a, 71b and 71c, the electrode set 72 comprises electrodes 72a, 72b and 72c, and so forth. The helical distal end portion 60 of the lead body carrying the electrode array 62 comprises, in the specific embodiment shown, three turns 81-83, each turn carrying eight electrodes, one from each set. Thus, the first helical turn 81 carries electrodes 71a-78a, the second helical turn 82 carries electrodes 71b-78b, and the third helical turn 83 carries electrodes 71c-78c. It will be seen that the electrode set 74, comprising electrodes 74a, 74b and 74c on the successive turns 81-83 of the helical lead body lie along a longitudinal line 84 extending along the length of the vein in the direction of blood flow; similarly, the electrode set 78 comprising electrodes 78a, 78b and 78c lie along a longitudinal line 86 also aligned with the direction of blood flow within the vein, and so forth, for the remaining electrode sets 71-73 and 75-77.

In one embodiment, each of the electrode sets 71-78 may be connected to form a double bipolar stimulation channel with corresponding electrodes of the various sets being electrically connected in parallel. By way of example, as best seen in FIG. 3, by way of illustration, the electrodes 71a-78a along the first turn 81 of the helical portion 60 are electrically connected in parallel to a first anodal contact 88 on the connector assembly 48 on the proximal end of the lead body, the electrodes 71b-78b along the second turn 82 of the helical portion 60 are electrically connected in a parallel to a cathodal contact 90 on the connector assembly 48 and the electrodes 71c-78c on the third turn 83 of the helical portion 60 are electrically connected to a second anodal contact 92 on the connector assembly 48. The polarities of the connector assembly contacts 88, 90 92 and therefore the polarities of the electrodes to which they are connected may, of course, be reversed so that the first and third contacts 88 and 92 are cathodal and the intermediate contact 90 is anodal. Further, all of the electrodes of all of the sets may be connected in parallel to provide a "unipolar" arrangement in which, for example, the electrodes are unipolar cathodal while the pulse generator casing or can comprises a common, electrode of complementary, anodal polarity.

It will be evident that electrodes along a given turn of the helical distal portion 60 of the lead body 40 may be equally spaced apart (45° for eight electrodes) or unequally spaced apart. Still further, the number of electrode sets may be greater or less than eight. For example, ten sets of electrodes may be provided with the electrodes along each turn of the helical distal portion appropriately spaced apart, for example, equiangulary at 36° intervals. Further yet, the helical distal portion 60 of the lead body 40 may comprise more or less than three full turns. Although not intended to limit the scope of the invention, at least three turns is preferred since a larger number of stimulation sites arranged generally linearly along the inner surface of the vena cava adjacent to and in alignment with the vagus nerve is generally more effective to improve the likelihood of stimulating parasympathetic cardiovagal branches of the vagus nerve to counteract arrhythmias and thereby restore autonomic nervous system balance.

The electrical conductors connecting the electrodes with the contacts on the connector assembly may comprise conventional multi-strand/multi-filar cable conductors or coil conductors each occupying a lumen of the preferred multilumen housing. The interconnection configuration of the electrodes is preferably such that the number of electrical conductors coupling the electrode array and the connector assembly is minimized so as to minimize the diameter of the lead body. For example, three electrical conductors 94, 96 and 98 are required in the double bipolar interconnection arrangement of FIG. 3. In a unipolar arrangement, with all of the electrodes connected in parallel to a single contact on the connector assembly, only one electrical conductor running the length of the lead body would be needed.

The process for placing the helical distal end portion 60 of the lead body 40 within the SVC 14 follows conventional practice. The lead body is very flexible and its housing may have, as already explained, a lumen for receiving a stylet or guidewire that may be used by the implanting physician to maneuver the electrode-bearing portion of the lead body into position within the vena cava under fluoroscopy or other lead body position monitoring technique. When inserted into the lead body 40, the stylet or guidewire will tend to straighten the helical distal end portion 60 to facilitate advancement and placement of the electrode array 62 within the vein. Once the lead body has been placed at the target location within the vein, the stylet or guidewire is withdrawn allowing the helical portion of the lead body to expand to its preformed configuration in which the helical portion frictionally engages the inner surface 24 of the wall 22 of the vein to anchor that portion.

In one embodiment, the electrodes of the array 62 may be hard-wired to predetermine the stimulation configuration. For example, the electrodes may be hard-wired in sets of three along the lines described above. In another embodiment, the electrodes would be neither hard-wired nor grouped into predetermined sets of electrodes but instead a combination of electrodes would be selected for optimal vagal stimulation, as further explained below.

As shown in broken lines in FIG. 1, the lead body 40 may further comprise a lead body section 100 extending distally from the distal end portion 60. The optional distal section 100, comprising an extension of the tubular housing 44, may carry a conventional complement of cardiac stimulating and/or sensing electrodes. For example, in the exemplary embodiment depicted in FIG. 1, the distal section 100 carries, in a bipolar arrangement, a tip pacing and/or sensing electrode 102 preferably in electrical communication with the apex 20 of the RV, a ring pacing and/or sensing electrode 104 disposed proximally of the tip electrode, and a pair of spaced-apart cardioverting and/or defibrillating electrodes 106 and 108 proximally of the ring electrode 102. The electrodes 106 and 108 may be placed within the RV 18 and the RA 16, respectively. The tubular housing along the distal section 100 of the lead body may include a plurality of outwardly projecting tines 110 positioned proximally of the ring electrode. As is well known in the art, these tines function to become interlocked in the trabeculi within the heart to inhibit displacement of the distal section once the lead is implanted. It will be understood that projecting fins, a screw-in helix (electrically active or inactive), or some other suitable anchoring means may be used instead of, or in addition to, the tines 110.

Figure 4:
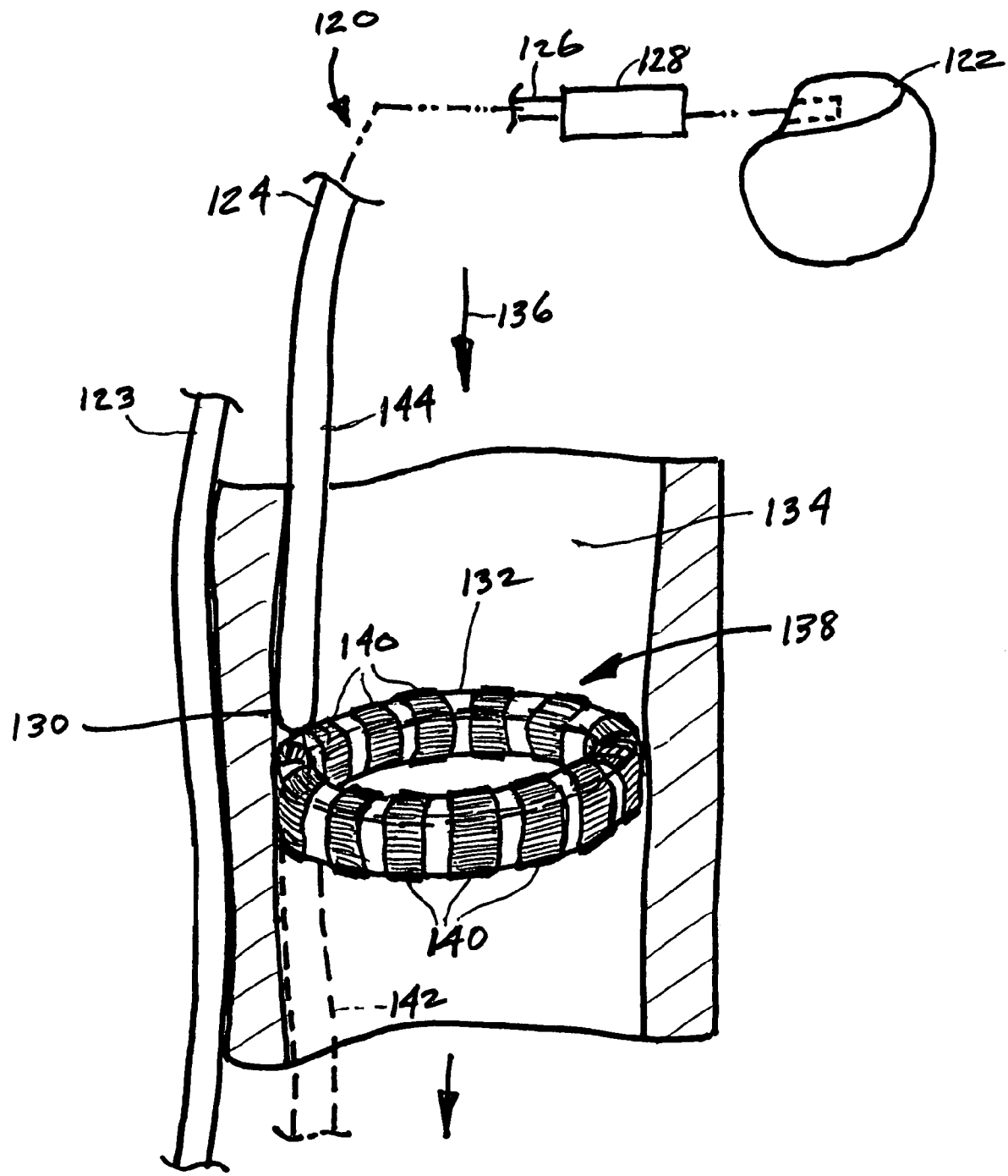
FIG. 4 is a diagrammatic, perspective view, along the lines of FIG. 2, showing a portion of a human heart having placed therein an endovascular, vagus nerve-stimulating lead in accordance with an alternative embodiment of the present invention.

FIG. 4 shows an alternative embodiment of the present invention comprising a lead 120 connectable to a pulse generator in the form of, for example, an implantable medical device 122 for delivering electrical stimulation signals to the vagus nerve 123. The lead 120 comprises a lead body 124 having a proximal end 126 carrying a connector assembly 128 receivable by the implantable medical device. Attached to a distal end 130 of the lead body 124 is a deployable annular member 132 that, when deployed within the SVC 134, lies generally in a plane perpendicular to the longitudinal direction of the vein, that is, the direction 136 of venous blood flow. The annular member 132 carries an electrode array 138 comprising a plurality of spaced-apart stimulating electrodes 140. The electrodes 140 may be equally spaced about the circumference of the annular member 132 or may be grouped into clusters or sets. By way of illustration, not restriction, a total of sixteen electrodes 140 equally spaced at 22.5° intervals may be provided. Alternatively, the sixteen electrodes may be grouped into four clusters of four electrodes each, the groups being spaced apart at 90° with the electrodes within each cluster being spaced 10° apart, and with the electrodes of each cluster being connected in parallel to a contact on the connector assembly 128 with a single electrical conductor.

It will be evident that the electrode array 138 may comprise more or less than sixteen electrodes; for example, the number of electrodes may be increased to thirty two or sixty four. The electrodes 140 may be electrically connected in a wide variety of ways. For example, all of the electrodes 140 may have the same polarity, anodal or cathodal, or the electrode polarities may alternate for bipolar operation. The electrodes may all have the same circumferential length and spaced apart by the same interelectrode gap, for example 5 mm long with a gap of 5 mm between adjacent electrodes. Alternatively, the electrode lengths and interelectrode gaps may vary.

As before, a distal section 142, carrying one or more stimulating and/or sensing electrodes for placement in the RA and/or RV, may extend distally from the distal end 130 of the lead body 124. Further, the lead body and optional distal section may comprise an insulating, outer, tubular sheath or housing 144, preferably multilumen, for containing electrical conductors connecting the electrodes 140 with corresponding contacts on the connector assembly 128.

A stylet-like tool may be used to steer the annular member 132 into position within the SVC under fluoroscopic observation. Once in position within the SVC, the stylet-like tool expands the member 132 so that its outer periphery engages the inner surface of the SVC wall to anchor the annular member and thus the lead body in place after which the stylet is withdrawn. During an implant of the lead body, the electrodes 140 may be energized in succession and heart activity monitored to determine which electrodes or combination of electrodes in the electrode array best capture the vagus nerve. The system may be arranged to be reprogrammable to maintain optimal stimulation during the life of the implant.

Figure 5:
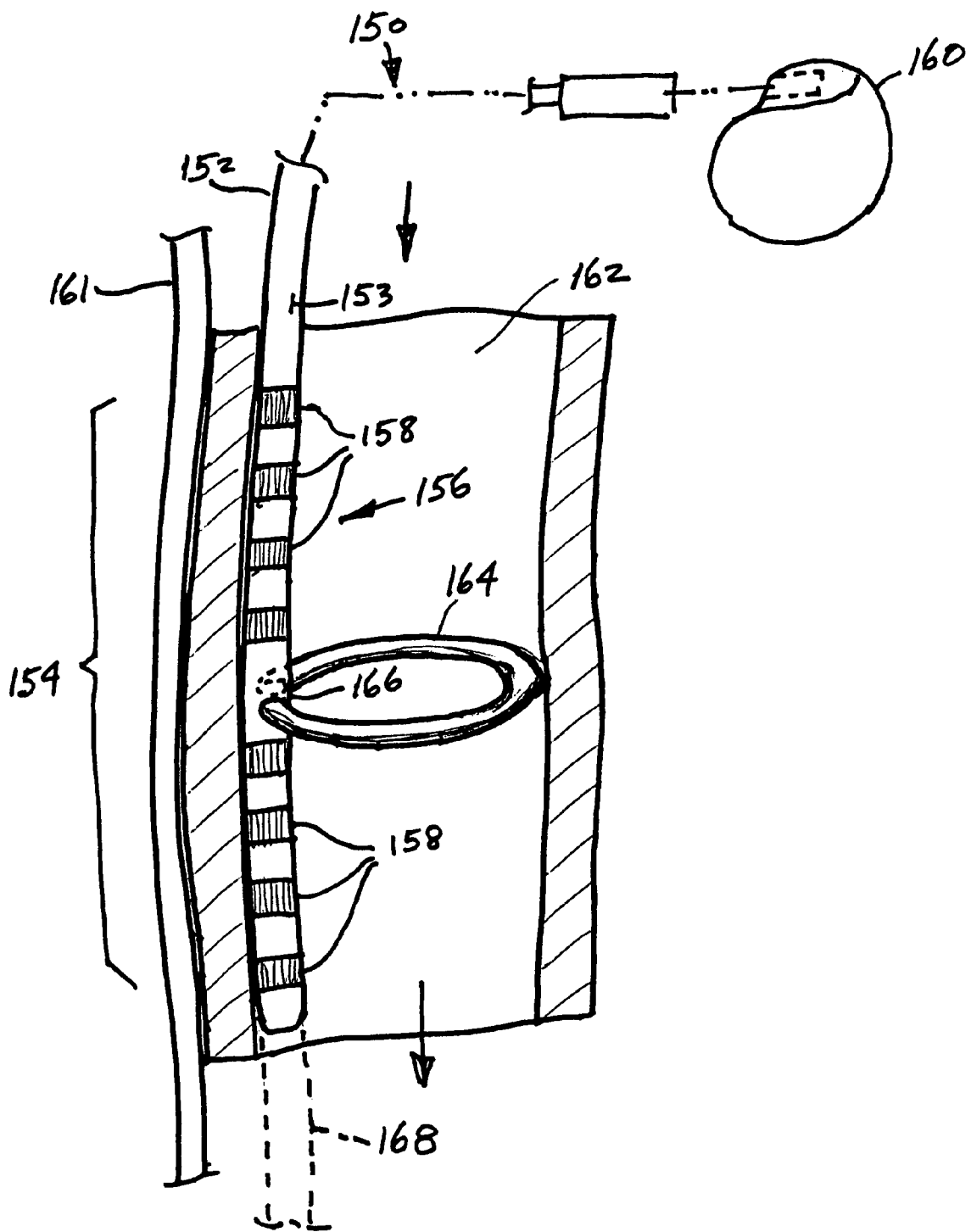
FIG. 5 is a diagrammatic, perspective view, along the lines of FIG. 2, showing a portion of a human heart having placed therein an endovascular, vagus nerve-stimulating lead in accordance with another alternative embodiment of the invention.

In a third specific, exemplary embodiment shown in FIG. 5, there is provided a lead 150 comprising a lead body 152 having an outer, insulating, preferably multilumen tubular housing 153 and a distal end portion 154 carrying a linear electrode array 156 comprising a plurality of electrodes 158, in this case, eight in number. The electrodes 158 are electrically connected to a signal generator such as an implantable pulse generator 160 for providing controlled electrical stimulation energy to the vagus nerve 161 via the plurality of electrodes 158 which are spaced apart along the length of the distal end portion 154 of the lead body 152. The electrodes 158 may have the same length, for example, 5 mm, with the same interelectrode gap between adjacent electrodes of, for example, 5 mm. Alternatively, the electrodes may have different lengths, may be non-uniformly spaced-apart, and may be grouped, for example, in pairs.

The distal end portion 154 of the lead body 152 is anchored in place within the SVC 162 by means of a deployable anchoring ring 164 that lies generally in a plane perpendicular to the direction of venous blood flow. The ring 164, which is secured to the lead body's distal end portion 154, preferably at a point 166 approximately midway between the ends of the portion 154, is expandable when deployed to engage the inner wall surface of the SVC 162. When fully expanded, the ring 164 urges the distal end portion 154 and the electrode array carried thereby into engagement with the inner wall of the SVC, preferably along the posterior thereof, opposite to, and in alignment with, the vagus nerve 161. The ring 164 may of the kind well-known for anchoring a stent deployed within a blood vessel.

Again, a distal section 168, carrying one or more stimulating and/or sensing electrodes for placement in the RA and/or RV, may extend distally from the distal end portion 154 of the lead body 152.

During placement of the leads of the various embodiments described herein, after the distal end or distal end portion has been positioned in the vein, the most suitable electrode combination that can capture the nerve is found in the following manner. Stimulus voltage is gradually increased and electrode pairs or triplets are sequentially selected. The intrinsic PR interval and ventricular rate are monitored continuously during this process. When a significant prolongation of the PR interval or reduction in ventricular rate is observed, the electrode combination providing that result is selected and programmed for stimulation. With lead systems depicted in FIGS. 1-4, the device may be made capable of re-evaluating the best electrode combination at a later time, automatically and periodically, to achieve most optimal stimulation site. This feature will enable the device to respond to slight changes in lead position over time so as to achieve successful stimulation at all times.

The vagal stimulation unit of the device can either be triggered by a prevention unit, a prediction trigger, a therapy trigger, or a discrimination algorithm. In the case of vagal stimulation for prevention, prediction, termination, and rate slowing, the stimulation may be turned on for a programmable interval or for a programmable number of short bursts that are triggered by each atrial activation. In the case of discrimination, there will be very low level stimulation applied to the nerve only to lengthen the PR interval without a need for high voltage levels to get complete AV block. The device is then able to determine whether a fast arrhythmia is being originated in the upper chambers and conducted through the AV node to the lower chambers or the arrhythmia is being originated in the lower chambers and there is no correlation with beats in the upper chambers.

While several illustrative embodiments of the invention have been shown and described, numerous variations and alternate embodiments will occur to those skilled in the art. Such variations and alternate embodiments are contemplated, and can be made without departing from the spirit and scope of the invention as defined in the appended claims.

What is claimed is:

1. An intravenous lead adapted to electrically stimulate fibers of the vagus nerve in a human patient, said nerve extending along an outer surface of the vena cava, the lead comprising:
    a lead body having a portion along the length thereof adapted to be placed within said vena cava, said portion of said lead body having a helical configuration and carrying an electrode array, said electrode array comprising at least eight sets of electrodes, each of said sets of electrodes comprising at least three electrodes adapted to engage an inner surface of said vena cava.

2. The lead of claim 1 wherein:
    said helical configuration comprises a plurality of turns, each of said turns carrying one of the electrodes of each of the sets of electrodes.

3. The lead of claim 2 wherein:
    the plurality of turns comprises three turns.

4. The lead of claim 2 wherein:
    the electrodes of each set of electrodes are adapted to be arranged in substantially longitudinal alignment when said portion of said lead body is placed within the vena cava.

5. The lead of claim 4 wherein:
    the electrodes comprising each set of electrodes are electrically connected to be alternately poled.

6. The lead of claim 4 wherein:
    each set of electrodes comprises three electrodes electrically connected in double bipolar fashion.

7. The lead of claim 1 wherein:
    said portion of said lead is preformed to provide the helical configuration.

8. The lead of claim 1 wherein:
    upon placement of said portion of said lead body in said vena cava, said portion of said lead body is expandable into said helical configuration to engage said inner surface of the vena cava vein so as to anchor said portion of the lead within the vena cava.

9. The lead of claim 1 further comprising:
    a distal section extending distally from said portion of the lead body, the distal section carrying at least one electrode selected from the group consisting of a tip pacing and/or sensing electrode, a ring pacing and/or sensing electrode, a cardioverting electrode and a defibrillating electrode.

10. An intravenous lead comprising a lead body having a portion along the length thereof for placement within the vena cava vein, said vein having a wall comprising an inner surface and an outer surface, said portion of said lead body having a helical configuration adapted to electrically stimulate fibers of the vagus nerve disposed adjacent to the outer surface of the wall of said vein, the lead body comprising:
    an array of electrodes disposed along said portion of the lead body, said electrode array comprising at least eight sets of electrodes, each of said sets of electrodes comprising at least three electrodes, the electrodes of each set being connected so as to be electrically energizable together independently of the electrodes of the remaining sets.

11. The lead of claim 10 wherein:

said portion of said lead is deployable within said vein to form a annular electrode array in electrical communication with the inner surface of the wall of the vein and lying in a plane substantially perpendicular to the direction of blood flow within the vein.

12. The lead of claim 10 wherein:

said portion of said lead is deployable within said vein to form a annular electrode array in engagement with the inner surface of the wall of the vein and lying in a plane substantially perpendicular to the direction of blood flow within the vein, said engagement anchoring said portion of the lead within said vein.

13. The lead of claim 10 wherein:

said portion of the lead has a generally annular shape adapted to lie in a plane substantially perpendicular to the direction of blood flow within the vein.

14. The lead of claim 13 wherein:

said portion of the lead is adapted to be brought into engagement with the inner surface of the wall of the vein so as to anchor said portion within said vein.

15. The lead of claim 10 wherein:

said portion of the lead has a helical shape.

16. The lead of claim 15 wherein:

said helical shape comprises a plurality of turns, each of said turns carrying one of the electrodes of each of the sets of electrodes.

17. The lead of claim 16 wherein:

the electrodes of each set of electrodes is arranged to be in longitudinal alignment.

18. The lead of claim 15 wherein:

the portion of the lead is preformed to provide the helical shape.

19. The lead of claim 15 wherein:

the helical shape is expandable into engagement with the inner surface of the wall of the vein to anchor said portion of the lead within the vein.

20. The lead of claim 10 further comprising:

a distal section extending distally from said portion of the lead body, the distal section carrying at least one electrode selected from the group consisting of a tip pacing and/or sensing electrode, a ring pacing and/or sensing electrode, a cardioverting electrode and a defibrillating electrode.

\* \* \* \* \*